(12) United States Patent
Hay

(10) Patent No.: US 6,953,443 B2
(45) Date of Patent: Oct. 11, 2005

(54) TIBIAL DISTRACTION DEVICE

(75) Inventor: Michael T. Hay, Irving, TX (US)

(73) Assignee: Imp Inc., Plainville, CT (US)

( * ) Notice: Subject to any disclaimer, the term of this patent is extended or adjusted under 35 U.S.C. 154(b) by 505 days.

(21) Appl. No.: 10/199,935

(22) Filed: Jul. 22, 2002

(65) Prior Publication Data

US 2004/0015114 A1 Jan. 22, 2004

(51) Int. Cl.$^7$ ................................................. A61F 5/00
(52) U.S. Cl. .......................... 602/33; 128/882; 5/648; 5/649
(58) Field of Search ............................ 602/32–36, 39, 602/40; 601/34, 33, 29, 24; 482/907, 140, 143; 5/648, 649, 650, 651; 128/882, 869

(56) References Cited

U.S. PATENT DOCUMENTS

| | | | | |
|---|---|---|---|---|
| 1,188,711 A | * | 6/1916 | Wilting | 602/39 |
| 1,904,942 A | * | 4/1933 | Ludwig | 602/35 |
| 1,950,948 A | * | 3/1934 | Murray | 606/242 |
| 2,768,622 A | * | 10/1956 | Sanders | 606/242 |
| 3,149,630 A | * | 9/1964 | Schmidt | 602/36 |
| 3,753,557 A | * | 8/1973 | Kelley | 5/648 |
| 4,166,459 A | * | 9/1979 | Nightingale | 602/35 |
| 4,602,619 A | * | 7/1986 | Wolf et al. | 606/241 |
| 4,627,423 A | * | 12/1986 | Kampner | 602/35 |
| 4,890,604 A | * | 1/1990 | Nelson | 602/32 |
| 5,002,046 A | * | 3/1991 | Scott | 602/36 |
| 5,020,525 A | * | 6/1991 | Ewing et al. | 602/27 |
| 5,025,802 A | * | 6/1991 | Laico et al. | 128/882 |
| 5,063,918 A | * | 11/1991 | Guhl | 602/40 |
| 5,290,220 A | * | 3/1994 | Guhl | 602/33 |
| 5,372,145 A | * | 12/1994 | Berger | 128/878 |
| 5,813,977 A | * | 9/1998 | Hinchliffe et al. | 600/183 |
| 5,881,730 A | * | 3/1999 | Burger | 128/878 |

\* cited by examiner

Primary Examiner—Michael A. Brown
Assistant Examiner—Huong Q. Pham

(57) ABSTRACT

A simple tibial distraction device includes a simple height-adjustable limb support triangle for positioning a patient's knee during surgery. The triangle includes a slidable support plate for carrying a Steinman pin, as well as a foot support strap to apply traction to the patient's lower leg and/or ankle.

5 Claims, 3 Drawing Sheets

TIBIAL DISTRACTION DEVICE

BACKGROUND OF THE INVENTION

The invention relates to apparatus for positioning a patient's limb for lower extremity surgery and the like.

A limb holding apparatus that mounts to an operating table for distracting the ankle of a patient for surgery and like procedures is found in U.S. Pat. No. 5,025,802 entitled "Surgical Holding Apparatus of Distracting Ankle" and U.S. Pat. No. 5,290,220 entitled "Non-Invasive Distraction System for Ankle Arthroscopy".

A system and related method for ankle arthroscopy distraction is described in U.S. Pat. No. 5,063,918 entitled "Multi-Mode Distraction for Ankle Arthroscopy".

Simple multi-functional Knee Positioning Triangles for supporting limbs for lower extremity surgery are obtainable from Innovative Medical Products, inc., Plainville, Conn.

Accordingly, it would be ergonomically advantageous to provide such knee positioning triangles with sufficient functionality to allow lower extremity surgery with the ability to apply traction to the ankle and without having to attach such triangles to the operating table, as here before required with the above-identified prior art.

One purpose of the invention is to describe an adjustable knee-positioning triangle having sufficient functionality to allow tibial and ankle surgery without requiring any such attachment to the operating table and be radiolucent while distracting from the ankle.

SUMMARY OF THE INVENTION

The invention comprises a tibial distraction device in the form of a height adjustable limb support triangle that includes a slidable support plate for carrying a Steinman pin or an ankle support strap. The device allows ankle surgery, tibial nailing as well as other surgical procedures in which traction through the ankle is required.

DESCRIPTION OF THE PREFERRED EMBODIMENT

Figure 1:
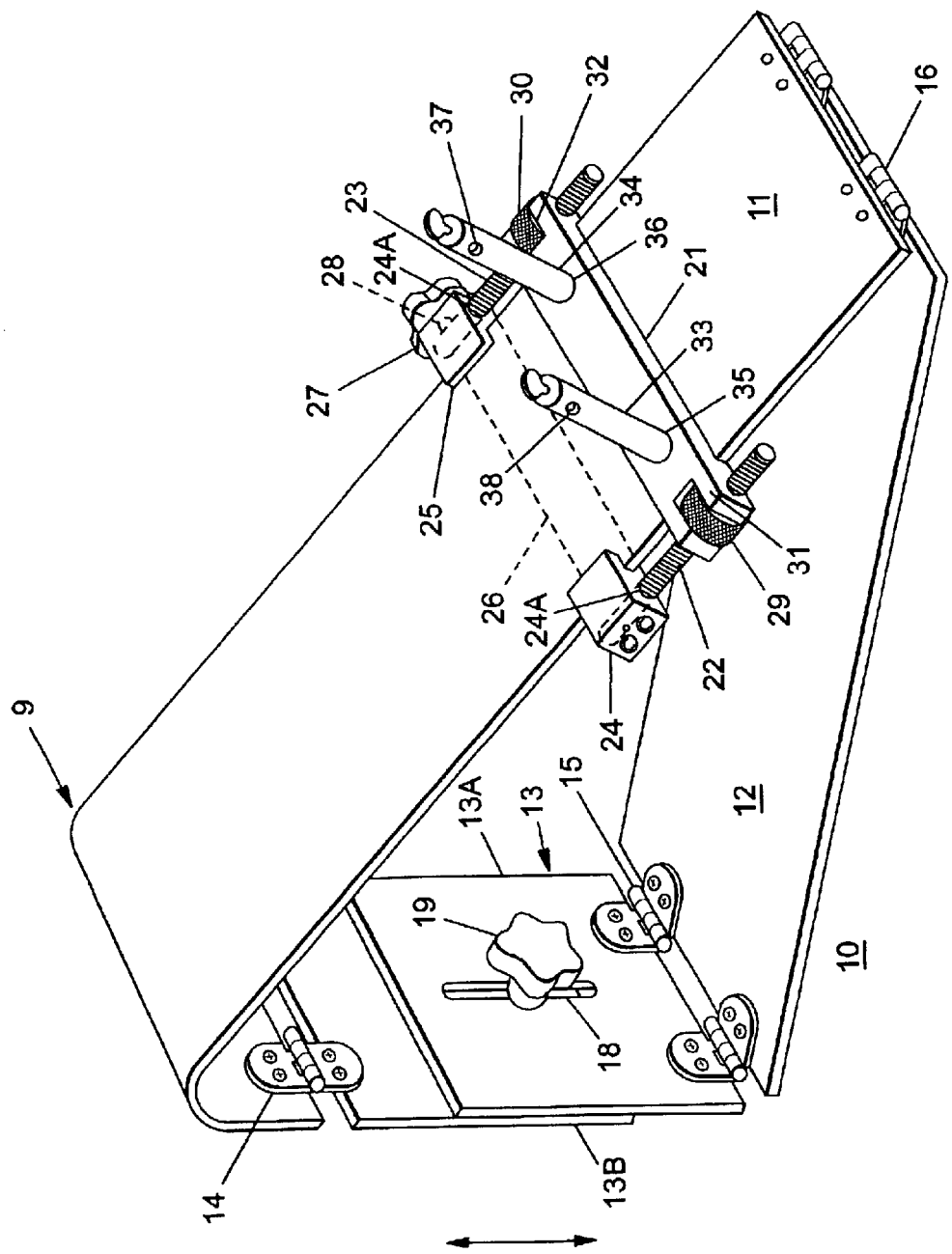
FIG. 1 is a top perspective view of the tibial distraction device in accordance with the invention.

The tibial distraction device, hereafter "device" 10 is shown in FIG. 1 to include a top plate 11 connected to a bottom plate 12 and to a side plate 13 by means of hinges 16 and 14. The side plate 13 is additionally connected to the bottom plate 12 by means of hinges 15. The height of the device is adjustable in the indicated vertical direction by the provision of a pair of plates 13A, 13B that are slidably arranged together by means of the adjustment knob 19 that attaches to a threaded rod 17 passing thru the elongated aperture 18 to the threaded nut 20 on the opposite surface of the plate 13B. To increase or decrease the height of the apex 9, at the top of the device 10, the knob 19 is rotated in the counterclockwise direction to loosen the threaded rod 17 from the nut 20 and the plate 13A is moved upwards or downwards, accordingly. When the appropriate height is selected, the knob 19 is rotated in the clockwise direction to tighten the threaded rod 17 within the nut 20.

The support plate 21 is positioned on the top plate 11 by means of a pair of opposing threaded rods 22, 23 that terminate at one end within the opposing apertured housings 24, 25 that are connected together on the opposite face of the top plate 21 by means of a plate 26. A pair of opposing knurled knobs 29, 30 threadingly engage the threaded rods 22, 23 and are positioned within the U-shaped apertures 31, 32 on the opposite ends of the top plate 11. An adjustment knob 27 is attached to a threaded rod 28 which extends within the threaded housing 25 and abuts against the top plate 11 to deter movement of the support plate. Both of the threaded rods 22, 23 extend within the apertures 24A, 24B in the associated housings 24, 25 in clearance relation to allow initial manual movement of the support plate 21 along the indicated direction along the top plate 11. Exact and precise positioning of the support plate in either direction is achieved by the clockwise or counter-clockwise rotation of the associated knobs 29, 30. A pair of upstanding Steinman pin support rods 33, 34 are positioned apart from each other on the support plate 21 and threadingly engage the support plate via threaded apertures 35, 36 at one end. The Steinman pin (not shown) is received at its opposite ends within the apertures 37, 38. A pair of threaded knobs extends within the top of the support rods 33, 34 to engage the ends of the Steinman pin to secure the pin therein.

Figure 2:
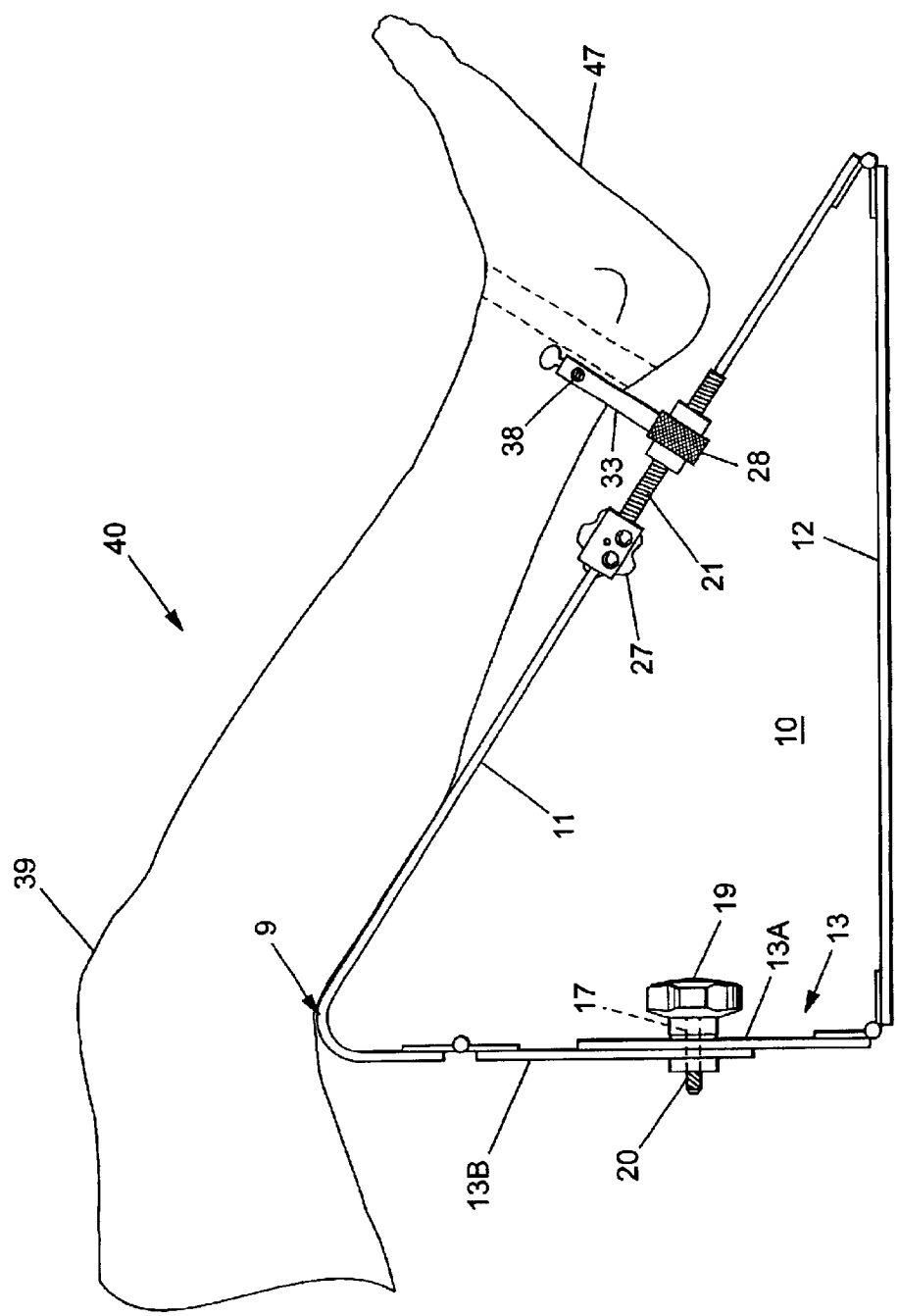
FIG. 2 is an enlarged side view of the tibial distraction device of FIG. 1 supporting a patient's knee, leg and foot during ankle surgery.

FIG. 2 depicts a patient's leg 40 supported on the tibial distraction device 10, according to the invention, with the apex 9 arranged under the patient's knee 39. As described earlier, the apex 9 is raised or lowered by rotating the knob 19 to loosen the threaded rod 17 from the bolt 20 thereby allowing the plate 13A to move relative to plate 13B to achieve the ideal height of the knee 39 depending on the intended operative procedure. The side plate 13 is then secured in the selected position by rotating the knob 19 to tighten the threaded rod 17 within the bolt 20. The patient's foot 47 is positioned within the pin support rods 33, 34 (FIG. 1) although only support rod 33 is depicted in FIG. 2, and the Steinmen pin (not shown) is inserted within the openings 37, 38 (FIG. 1) although only opening 38 is depicted in FIG. 2. The position of the foot 47 relative to the knee 39 is first adjusted by loosening the knob 27 on the support plate 21 and manually moving the support plate in either direction before tightening the knob 27. Precise positioning of the foot is obtained by then rotating the knurled knobs 29, 30 (FIG. 1) although only knob 29 is depicted in FIG. 2.

Figure 3:
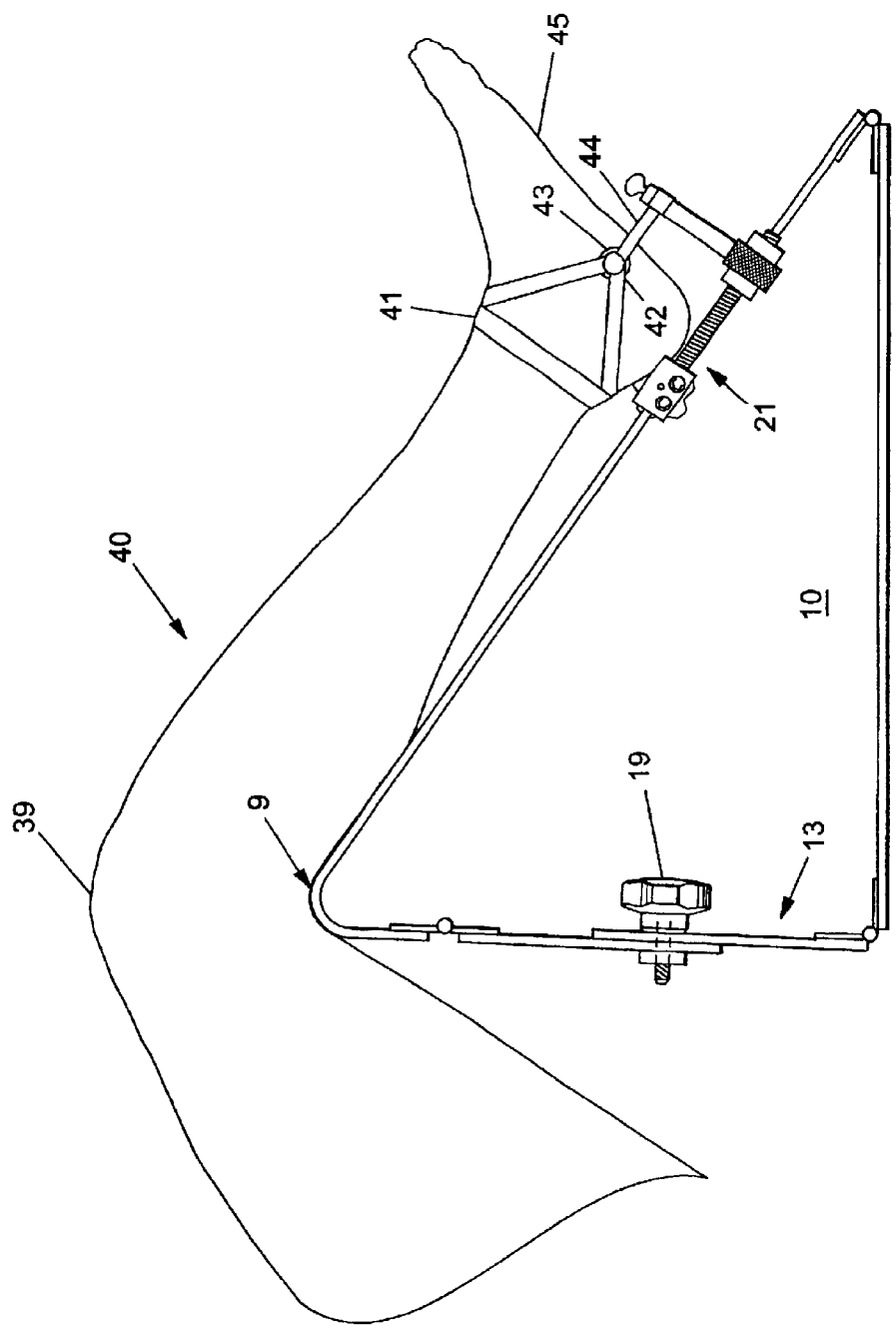
FIG. 3 is an enlarged side view of the tibial distraction device of FIG. 1 supporting a patient's knee, leg and foot during ankle traction with an ankle strap.

FIG. 3 depicts a patient's leg 40 supported on the tibial distraction device 10, according to the invention, with the apex 9 arranged under the patient's knee 39. The apex 9 is adjusted via the side plate 13 for optimum position of the knee 39 and foot 45 to perform ankle traction. In further accordance with the invention a strap 41, that attaches to a ring 42 at one end, is positioned around the foot 45. The hook 43 attaches to the pin support rods 33, 34 (FIG. 1) by a corresponding pair of cords, although only one cord 44 is shown herein. The support plate 21 is then moved in the manner described earlier with reference to FIG. 2 for optimum positioning of the foot 45 to apply traction to the patient's lower leg and/or ankle.

A device for positioning a patient's leg, knee and foot for tibial distraction in the form of a height adjustable limb support triangle that includes a slidable support plate for carrying a Steinman pin, as well as an ankle support strap has herein been described.

What is claimed is:

1. An adjustable limb positioning device comprising:
   a top plate having first and second ends;
   a support plate movebly arranged on said top plate;
   a pair of apertured housings positioned on opposite sides of said top plate;
   a bottom plate having first and second ends;
   a first side plate having first and second ends and a second side plate having first and second ends, said first and second side plates being slidably connected together;
   said first end of said top plate being hingebly connected with said first end of said bottom plate and said second end of said top plate being hingebly connected with said first end of said first side plate;
   said second end of said bottom plate being hingebly connected with said first end of said second side plate;
   a first threaded rod extending through said first and second side plates, said first threaded rod terminating at a first knob on said first side plate, said first threaded rod terminating at a nut on said second side plate;
   a pair of second knobs retained within opposite sides of said support plate and a pair of second threaded rods extending between said second knobs and said apertured housings for providing means for movement of said support plate along said top plate;
   whereby movement of said first side plate relative to said second side plate changes a separation distance defined between said first end of said top plate and said second end of said bottom plate.

2. The device of claim 1 including a third knob attached to a third threaded rod, said third threaded rod extending within one of said apertured housings into abutment with one of said second threaded rods.

3. An adjustable limb positioning device comprising:
   a top plate having first and second ends;
   a support plate movebly arranged on said top plate;
   a pair of apertured housings positioned on opposite sides of said top plate;
   a bottom plate having first and second ends;
   a first side plate having first and second ends and a second side plate having first and second ends, said first and second side plates being slidably connected together;
   said first end of said top plate being hingebly connected with said first end of said bottom plate and said second end of said too plate being hingebly connected with said first end of said first side plate;
   said second end of said bottom plate being hingebly connected with said first end of said second side plate;
   a first threaded rod extending through said first and second side plates, said first threaded rod terminating at a first knob on said first side plate, said first threaded rod terminating at a nut on said second side plate;
   a pair of second knobs retained within opposite sides of said support plate and a pair of second threaded rods extending between said second knobs and said apertured housings for providing means for movement of said support plate along said top plate;
   whereby movement of said first side plate relative to said second side plate changes a separation distance defined between said first end of said top plate and said second end of said bottom plate and wherein said second threaded rods extend within said apertured housings in clearance relation.

4. The device of claim 1 wherein said first threaded rod extends within a first extended aperture in said first side plate and extends within a second extended aperture of said second side plate.

5. The device of claim 1 further including means for supporting a support strap.

* * * * *